United States Patent
Choi et al.

(10) Patent No.: US 10,156,553 B2
(45) Date of Patent: Dec. 18, 2018

(54) ELECTRONIC DEVICE WITH SENSOR PORTS HAVING ENHANCED AIRFLOW

(71) Applicant: Apple Inc., Cupertino, CA (US)

(72) Inventors: Hyuk J. Choi, Pleasanton, CA (US); Roberto M. Ribeiro, San Jose, CA (US)

(73) Assignee: Apple Inc., Cupertino, CA (US)

( * ) Notice: Subject to any disclaimer, the term of this patent is extended or adjusted under 35 U.S.C. 154(b) by 258 days.

(21) Appl. No.: 15/085,862

(22) Filed: Mar. 30, 2016

(65) Prior Publication Data

US 2017/0284987 A1 Oct. 5, 2017

(51) Int. Cl.
*G01N 33/00* (2006.01)

(52) U.S. Cl.
CPC .............................. *G01N 33/0009* (2013.01)

(58) Field of Classification Search
CPC ........... G01N 33/0009; G01N 33/0004; G01D 11/245
See application file for complete search history.

(56) References Cited

U.S. PATENT DOCUMENTS

| 8,047,071 | B2 | 11/2011 | Jia |
| 2014/0134053 | A1* | 5/2014 | Mayer .................. G01N 33/497 422/83 |
| 2014/0193018 | A1 | 7/2014 | Lim et al. |
| 2015/0226585 | A1 | 8/2015 | Yang |

FOREIGN PATENT DOCUMENTS

| EP | 2733484 | 5/2014 |
| EP | 2905673 | 1/2016 |

* cited by examiner

*Primary Examiner* — Blake A Tankersley
(74) *Attorney, Agent, or Firm* — Treyz Law Group, P.C.; G. Victor Treyz; David K. Cole

(57) ABSTRACT

An electronic device may have input-output devices such as sensors. The sensors may include environmental sensors that make measurements on the environment surrounding the electronic device. The environmental sensors may make measurements such as temperature measurements, humidity measurements, gas composition measurements, and particulate level measurements. A sensor may communicate with external air through a sensor port in an electronic device housing. An electronic device may have a movable member. The movable member may be moved in response to motion of the electronic device when handled by user or motion of a button or other movable member that is actuated by the user. As the movable member moves, the movable member may create enhanced airflow through the sensor port. This may refresh the air adjacent to an environmental sensor and enhance sensor response time.

20 Claims, 10 Drawing Sheets

ELECTRONIC DEVICE WITH SENSOR PORTS HAVING ENHANCED AIRFLOW

FIELD

This relates generally to electronic devices and, more particularly, to electronic devices with sensors.

BACKGROUND

Electronic devices sometimes contain sensors. Sensors may be used, for example, to make temperature measurements or other measurements on the ambient environment in which an electronic device is being operated.

If care is not taken, sensor performance may be adversely affected by poor coupling between a sensor and the external environment. An electronic device may have a sensor port with structures that helps protect a sensor from environmental contaminants. These structures directly impact the environmental coupling with the sensor in the device. This can lead to undesirably slow sensor response times.

SUMMARY

An electronic device may have input output devices such as sensors. The sensors may include environmental sensors that make measurements of the environment surrounding the electronic device. The environmental sensors may make measurements such as temperature measurements, humidity measurements, gas composition measurements, and particulate level measurements.

A sensor such as an environmental sensor may communicate with external air through a sensor port in an electronic device housing. An electronic device may have a movable member. The movable member may be moved relative to the electronic device housing. The movable member may be moved in response to motion of the electronic device when handled by user or in response to motion of a button or other movable member that is actuated by the user.

As the movable member moves within the device, the movable member may create enhanced airflow through the sensor port. This may refresh the air adjacent to an environmental sensor and enhance sensor response time.

DETAILED DESCRIPTION

Electronic devices may be provided with sensors. The sensors in an electronic device may include one or more sensors that make measurements on the environment in which the electronic device is operated. For example, sensors may make measurements on ambient air temperature, the chemical composition of the air and the particulate count in the air, air humidity, and other measurement on the air around the device. Because sensors such as these make measurements on the environment surrounding the electronic device, the sensors may sometimes be referred to as environmental sensors.

Figure 1:
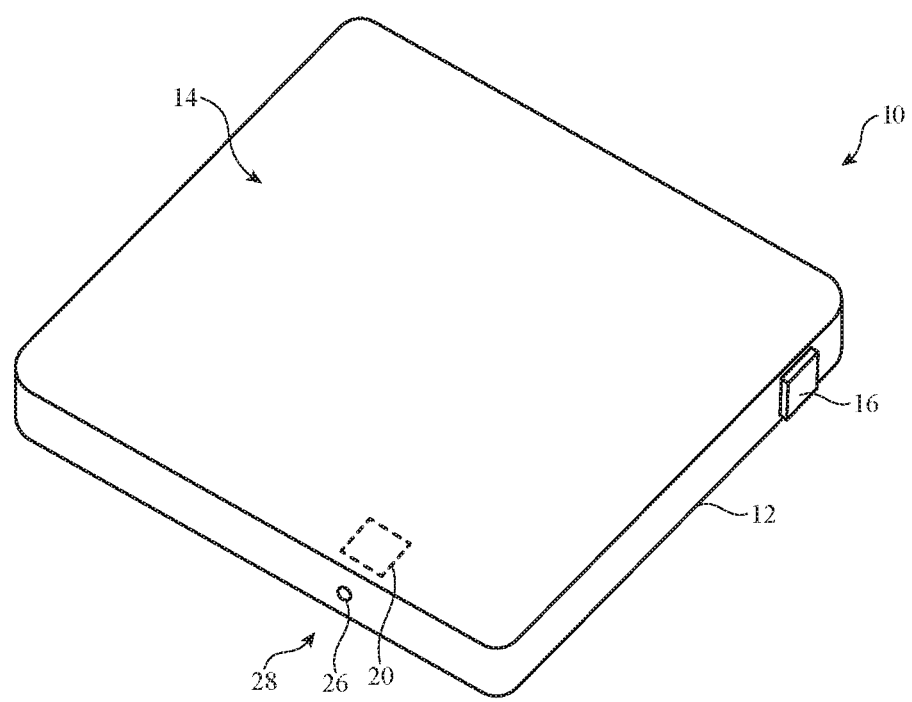
FIG. 1 is a perspective view of an illustrative electronic device in accordance with an embodiment.

FIG. 1 is a perspective view of an illustrative electronic device of the type that may include environmental sensors. Electronic device 10 may be a computing device such as a laptop computer, a computer monitor containing an embedded computer, a tablet computer, a cellular telephone, a media player, or other handheld or portable electronic device, a smaller device such as a wrist-watch device, a pendant device, a headphone or earpiece device, a device embedded in eyeglasses or other equipment worn on a user's head, or other wearable or miniature device, a television, a computer display that does not contain an embedded computer, a gaming device, a navigation device, an embedded system such as a system in which electronic equipment with a display is mounted in a kiosk or automobile, equipment that implements the functionality of two or more of these devices, an accessory (e.g., earbuds, a remote control, a wireless trackpad, etc.), or other electronic equipment. In the illustrative configuration of FIG. 1, device 10 is a portable device such as a cellular telephone, media player, tablet computer, wrist-watch device or other portable computing device. Other configurations may be used for device 10 if desired. The example of FIG. 1 is merely illustrative.

In the example of FIG. 1, device 10 includes display 14. Display 14 has been mounted in housing 12. Electronic device housing 12, which may sometimes be referred to as an enclosure or case, may be formed of plastic, glass, ceramics, fiber composites, metal (e.g., stainless steel, aluminum, etc.), other suitable materials, or a combination of any two or more of these materials. Housing 12 may be formed using a unibody configuration in which some or all of housing 12 is machined or molded as a single structure or may be formed using multiple structures (e.g., an internal frame structure, one or more structures that form exterior housing surfaces, etc.).

Display 14 may be a touch screen display that incorporates a layer of conductive capacitive touch sensor electrodes or other touch sensor components (e.g., resistive touch sensor components, acoustic touch sensor components, force-based touch sensor components, light-based touch sensor components, etc.) or may be a display that is not touch-sensitive. Capacitive touch sensor electrodes may be formed from an array of indium tin oxide pads, other transparent conductive structures, or other touch sensor electrode structures.

Display 14 may include an array of pixels formed from liquid crystal display (LCD) components, an array of electrophoretic pixels, an array of plasma display pixels, an array of organic light-emitting diode pixels or other light-emitting diode pixels, an array of electrowetting pixels, or pixels based on other display technologies.

Display 14 may be protected using a display cover layer such as a layer of transparent glass, clear plastic, transparent ceramic, sapphire or other transparent crystalline material, or other transparent layer(s). The display cover layer may have a planar shape, a convex curved profile, a concave curved profile, a shape with planar and curved portions, a layout that includes a planar main area surrounded on one or more edge portions that are bent out of the plane of the planar main area, or other suitable shape. Openings may be formed in the display cover layer to accommodate one or more buttons, a speaker port, etc.

Openings may also be formed in housing 12. For example, opening 26 may be formed through housing 12 to form sensor port 28. Environmental sensor 20 may be mounted within the interior of housing 12 in alignment with sensor port 28. Air from the exterior of device 10 may flow through opening 26 to reach environmental sensor 20 and particles, humidity, gases, and heat associated with exterior air may diffuse or otherwise pass into the vicinity of sensor 20 through opening 26. Environmental sensor 20 may be a sensor that measures temperature, that measures relative humidity, that measures ozone concentration, that measures $CO_2$ concentration, or that measures other chemical properties of the ambient air surrounding device 10, that measures particulates in the air, or that measures other characteristics of the ambient air. One or more buttons such as illustrative button 16 may be formed from movable button members that are mounted within respective openings in device 10 (housing 12). If desired, openings may also be formed in the wall of housing 12 and/or display 14 for connector ports, acoustic ports, etc.

Figure 2:
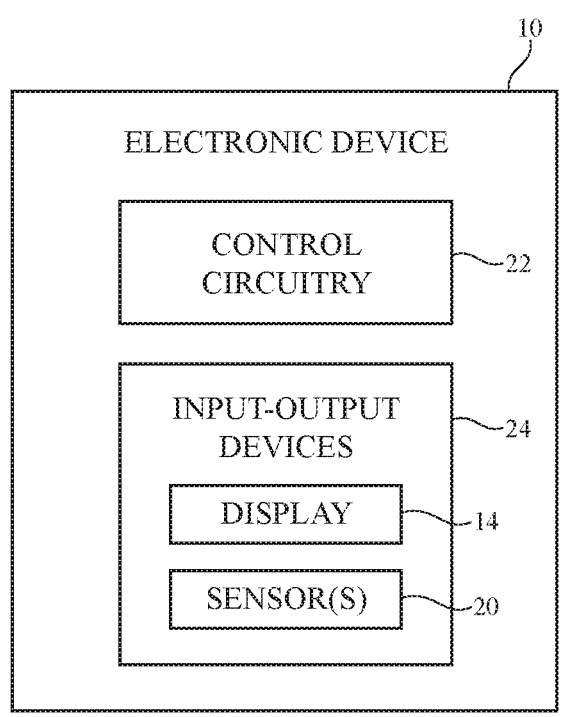
FIG. 2 is a schematic diagram of an illustrative electronic device with sensors in accordance with an embodiment.

FIG. 2 is a schematic diagram of an illustrative electronic device with one or more sensors that make measurements on ambient air through sensor ports such as sensor port 28. As shown in FIG. 2, electronic device 10 may have control circuitry 22. Control circuitry 22 may include storage and processing circuitry for supporting the operation of device 10. The storage and processing circuitry may include storage such as hard disk drive storage, nonvolatile memory (e.g., flash memory or other electrically-programmable-read-only memory configured to form a solid state drive), volatile memory (e.g., static or dynamic random-access-memory), etc. Processing circuitry in control circuitry 22 may be used to control the operation of device 10. For example, the processing circuitry may display alerts, may display sensor measurement data, and may take other suitable actions in response to temperature measurements, ambient air gas composition measurements, ambient air particulate measurements, ambient air relative humidity measurements, etc. The processing circuitry may be based on one or more microprocessors, microcontrollers, digital signal processors, baseband processors, power management units, audio chips, application specific integrated circuits, etc.

Input-output circuitry in device 10 such as input-output devices 24 may be used to allow data to be supplied to device 10 and to allow data to be provided from device 10 to external devices. Input-output devices 24 may include buttons such as button 16 and other buttons, joysticks, scrolling wheels, touch pads, key pads, keyboards, microphones, speakers, tone generators, vibrators or other components with moving parts, cameras, light-emitting diodes and other status indicators, data ports, etc. As shown in FIG. 2, input-output devices 24 may include sensors 20. Sensors 20 may include environmental sensors such as sensors that make temperature measurements, ambient air gas composition measurements, ambient air particulate measurements, ambient air relative humidity measurements, etc. If desired, input-output devices 24 may include sensors such as force sensors, magnetic sensors, proximity sensors, touch sensors, light sensors, acoustic sensors, and other sensors. A user can control the operation of device 10 by supplying commands through input-output devices 24 and may receive status information and other output from device 10 using the output resources of input-output devices 24. Input-output devices 24 may include one or more displays such as display 14.

Control circuitry 22 may be used to run software on device 10 such as operating system code and applications. During operation of device 10, the software running on control circuitry 22 may display images on display 14 using an array of pixels in display 14. The software running on control circuitry 22 may gather sensor data from sensors 20 such as temperature measurements, humidity measurements, gas concentration measurements, particulate counts, and other information on the characteristics of the air surrounding device 10 (sometimes referred to as air readings or environmental sensor information).

Figure 3:
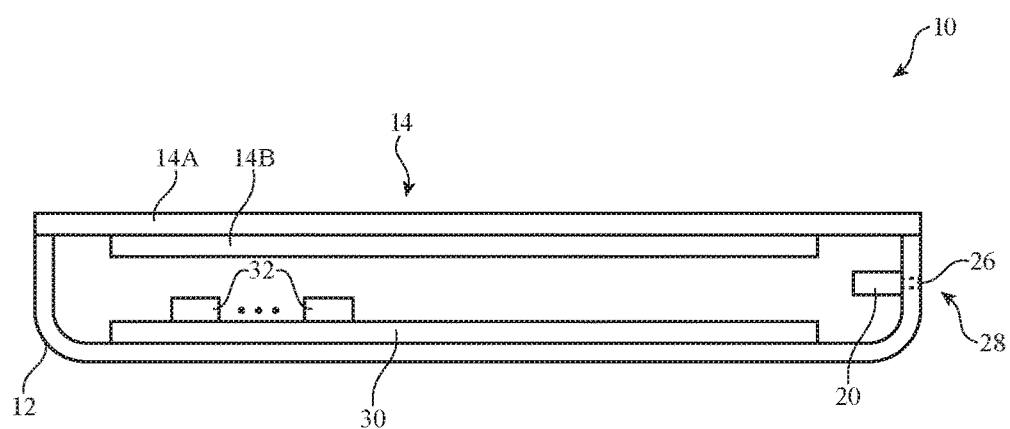
FIG. 3 is a cross-sectional side view of an illustrative electronic device in accordance with an embodiment.

FIG. 3 is a cross-sectional side view of an illustrative device with an environmental sensor. As shown in the example of FIG. 3, device 10 may include a display such as display 14 mounted in housing 12. Display 14 may have display layers 14B (e.g., a liquid crystal display module, an organic light-emitting diode display, or other layers having an array of pixels to display images) and may have an optional protective outer layer such as transparent display cover layer 14A. Electrical components 32 (e.g., integrated circuits and other devices for forming control circuitry 22 and/or input-output devices 24) may be mounted on one or more substrates such as substrate 30 (e.g., a flexible printed circuit substrate formed from a flexible layer of polyimide or a sheet of other flexible polymer or a rigid printed circuit board substrate formed from a rigid printed circuit board material such as fiberglass-filled epoxy). Housing 12 may have an opening such as opening 26 to form sensor port 28. If desired, opening 26 may be formed through display layer 14A or other structure in device 10. Environmental sensor 20 may be mounted within the interior of housing 12 and may make measurements of the environment surrounding device 10 through opening 26.

Figure 4:
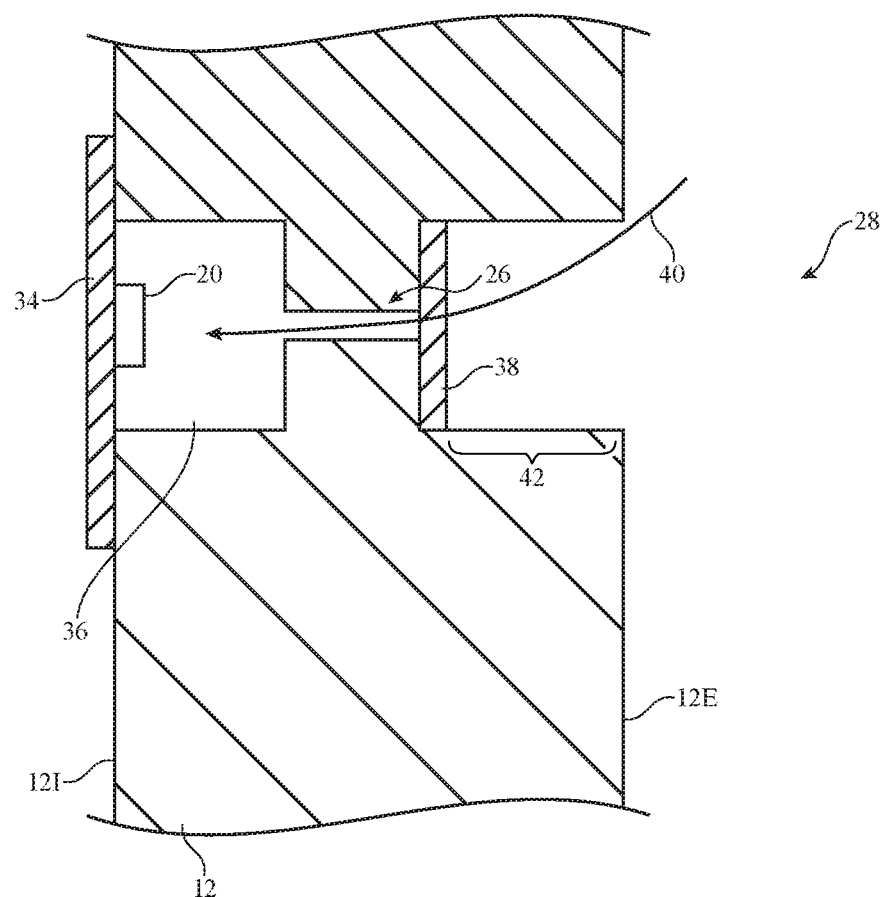
FIG. 4 is a cross-sectional side view of an illustrative housing wall with a sensor port and associated sensor in accordance with an embodiment.

An illustrative configuration for mounting sensor 20 in communication with sensor port 28 is shown in FIG. 4. As shown in FIG. 4, housing 12 may have a wall with exterior surface 12E and opposing interior surface 12I. The external ambient environment surrounding device 10 (i.e., external air) may be monitored by sensor 20 in device 10 through port 28 as indicated by path 40. Port 28 may be formed from a passageway through housing 12 of any suitable shape. In the illustrative example of FIG. 4, port 28 has an exterior recessed portion such as portion 42 (which may have one or more holes or other openings), a porous contaminant-blocking structure such as structure 38 (e.g., a thin layer of wire and/or plastic mesh, a porous membrane, multiple layers of plastic and/or metal structures with openings, etc.). Porous structure 38 and the shape of the passageway(s) associated with port 28 may help prevent moisture, dust, and other contaminants from entering the interior of device 10 and thereby interfering with the operation of sensor 20.

Sensor 20 may be mounted on a flexible or rigid printed circuit (see, e.g., printed circuit 34) or other substrate and may be located in cavity 36 (e.g., a cavity in housing 12). Cavity 36 may communicate with the exterior of device 10 via channel 26. Cavity 36 and channel 26 may have other shapes (e.g., curved shapes, shapes formed from multiple smaller openings, etc.). The cross-sectional shapes of the opening(s) through the wall of housing cavity 36 associated with sensor port 28 may be rectangular, square, circular, or oval, may have a combination of straight and curved edges, or may have any other suitable shapes. Porous structure 38 and/or other structures for preventing the intrusion of contaminants into device 10 and cavity 36 may be located before or after channel 26, may be placed over exterior surface 12E of housing 12, or may be located elsewhere within sensor port 28. The example of FIG. 4 is merely illustrative.

Channel 26, porous structure 38, and cavity 36 are preferably configured to prevent intrusion of contaminants into device 10 that could interfere with the operation of sensor 20. For example, to prevent intrusion of contaminants, channel 26 should not be too short or too wide, cavity 36 should not be too small, and the porosity of structure 38 should not be too high. At the same time, if channel 26 is too long, cavity 36 is too large, and/or the porosity of structure 38 is too low, it may take an undesirably long time for sensor 20 to measure changes in temperature, humidity, gas composition, and/or particulate count or other characteristics of the air surrounding device 10 (e.g., because communication between sensor 20 and the exterior of device 10 through port 28 is overly restricted).

To enhance communication of sensor 20 with the external environment through sensor port 28, device 10 may be provided with moving structures that enhance the environmental coupling through port 28. By refreshing the air within cavity 36, the response time of sensor 20 to changes in the external environment of device 10 may be reduced.

Figure 5:
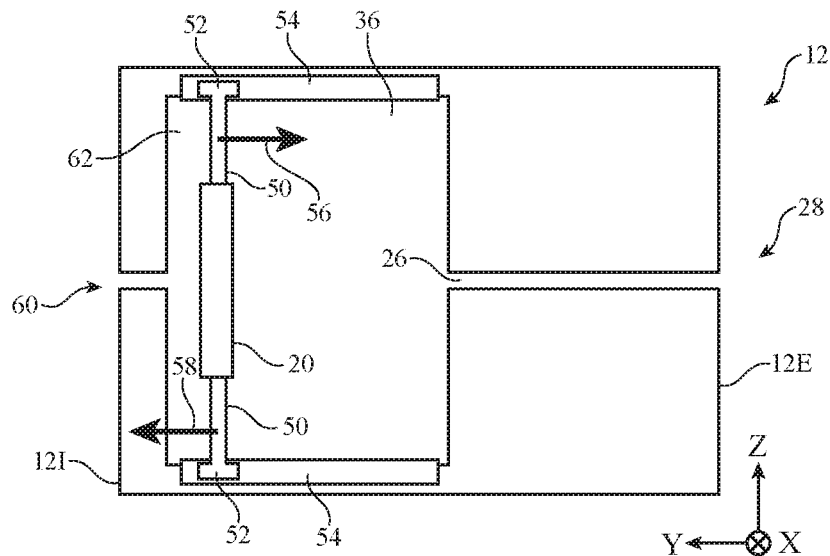
FIG. 5 is a cross-sectional side view of an illustrative housing wall in which a movable member such as a movable sensor support structure has been provided to enhance airflow through a sensor port in the wall in accordance with an embodiment.

An illustrative configuration for providing device 10 with a moving structure that enhances airflow through sensor port 28 is shown in the side cross-sectional view of port 28 of FIG. 5. As shown in FIG. 5, port 28 may include channel 26 and cavity 36 (porous structure 38 is not shown in the illustrative configuration of FIG. 5 and some of the other FIGS., but may be included in sensor port 28 as shown in FIG. 4). Sensor 20 may be mounted on sliding (moving) support member 50 (e.g., a rectangular sliding plate, a moving wall of other shapes, or other movable support structure). Moving support member 50 may have protrusions or other engagement features that engage with mating engagement features in housing 12 such as grooves 54 or other recesses. As the orientation of device 10 changes during use and handling of device 10 by a user, gravity and forces from the structures within device 10 will impart forces on member 50 (and on sensor 20 on member 50), thereby causing member 50 to move back and forth relative to housing 12, as shown by arrows 56 and 58.

Movement of member 50 relative to housing 12 (and cavity 36) causes pressure variations in the air within cavity 36 and thereby causes air to flow in and out of cavity 36 through channel 26. When, for example, member 50 moves in outward direction 56, stale air in cavity 36 will be expelled from cavity 36 to the exterior of device 10 through channel 26 and other passageways associated with port 28. When member 50 moves in inward direction 58, fresh air will be drawn into cavity 36 adjacent to sensor 20 through channel 26 and other portions of port 28. Accordingly, movement of member 50 due to movement of housing 12 from handling of device 10 by a user will help refresh the air within cavity 36 and will help lower the response time of sensor 20.

Member 50 may divide an interior volume in housing 12 (or other portion of device 10) into sensor cavity 36 (e.g., the portion the interior volume containing air that is sampled by sensor 20 and that communicates with the exterior of device 10 through port 28) and rear cavity '62. If desired, pressure relief passageways may be formed in device 10 so that backpressure does not develop in rear cavity 62 that could otherwise hinder the motion of member 50. Sensor cavity 36 and rear cavity 62 are preferably sealed off from each other by wall 50 so that the environment in sensor cavity 36 is influenced by the external environment and not internal air from rear cavity 62. In the example of FIG. 5, opening 60 in housing 12 vents air in cavity 62 to the interior of device 10 and thereby prevents backpressure from developing behind moving wall 50 when wall 50 moves in inwards direction 58. If desired, pressure relief passageways such as opening (passageway) 60 may vent to the exterior of device 10 or other locations. The example of FIG. 5 is merely illustrative.

Figure 6:
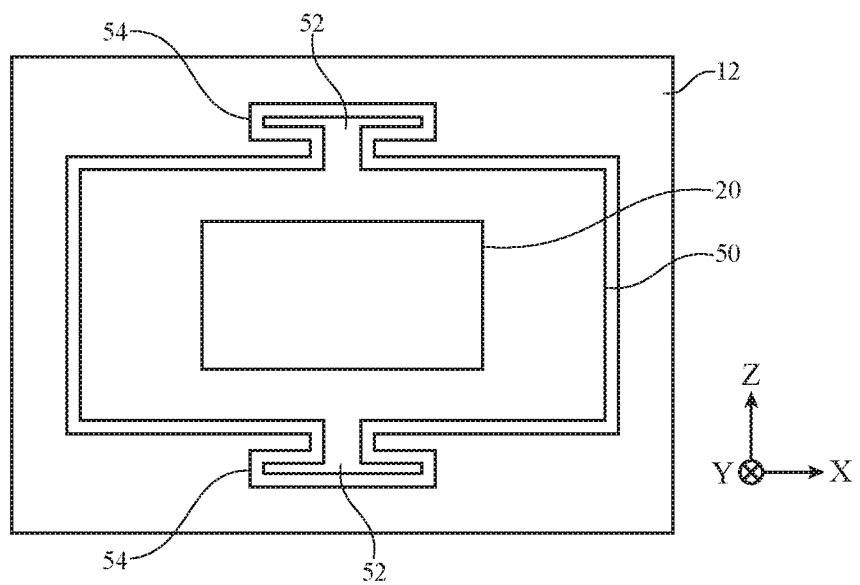
FIG. 6 is another cross-sectional view of the housing wall and movable sensor structure of FIG. 5 in accordance with an embodiment.

FIG. 6 is a front cross-sectional view of the structures of FIG. 5 showing how engagement features 52 may be formed from T-shaped protrusions that ride within grooves 54 in housing 12. This allows member 50 to move back and forth along the Y-axis of FIGS. 5 and 6 (e.g., inwardly and outwardly relative to the interior of device 10). Other arrangements may be used to allow gravity and changes in the orientation of device 10 to impart movement to moving structures in device 10 such as moving member 50 (e.g., configurations with supplemental weights to overcome friction, configurations with springs and/or gears to translate motion of a weight to motion of member 50, configurations in which the motion of member 50 involves rotation around a pivot point or other non-sliding motion, configurations in which multiple members move within device 10, configurations in which some or all of the passageways and mounting structures associated with housing 12 are formed from structures inside and/or outside of the main wall of housing 12, etc.). The configuration of FIGS. 5 and 6 is shown as an example.

If desired, weights (e.g., metal members) may be formed as integral portions of moving member 50 and/or may be attached to moving member 50 (e.g., in scenarios in which member 50 is formed from a substrate such as a printed circuit). This additional weight may help ensure that member 50 moves satisfactorily during handling of device 10 by a user.

Figure 7:
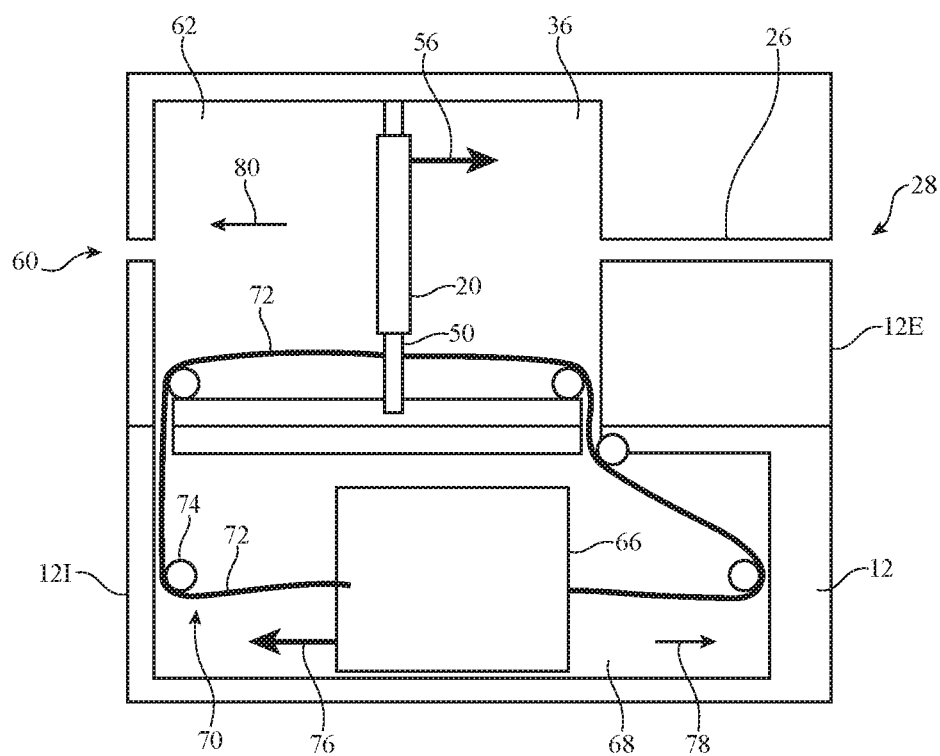
FIG. 7 is a cross-sectional side view of an illustrative housing wall with a movable member and associated moving mass that is moved in response to motion of an electronic device during handling by a user to help move the member and thereby enhance airflow through a sensor port in the wall in accordance with an embodiment.

FIG. 7 is a cross-sectional side view of housing 12 in a configuration in which motion of moving member 50 is promoted by movement of moving weight 66. Moving weight 66 may be formed from a metal member or other dense structure that moves within moving weight chamber 68. Moving weight 66 may be mechanically coupled to member 50 using a coupling structure such as coupling structure 70. Coupling structure 70 may include a flexible structure such as flexible member 72 (e.g., a strand of material, a belt, etc.) and guide structures such as pulleys 74 and/or other mechanical coupling structures to mechanically couple weight 66 to member 50. When device 10 is moved (e.g., when the orientation of device 10 and housing 12 shifts due to movement of device 10 during use by a user of device 10), weight 66 will be moved by gravity and/or force imparted onto weight 66 from the walls of chamber 68. Weight 66 will therefore move. The mass of weight 66 may be relatively large (e.g., larger than the mass of member 50) so that movement of weight 66 is sufficiently forceful to overcome system friction and thereby facilitate movement of member 50. In the example of FIG. 7, movement has been imparted to weight (mass) 66 in direction 76, which, via coupling structure 70, imparts movement to member 50 and sensor 20 in direction 56. When weight 66 is moved in direction 78, member 50 will be moved inwardly in direction 80, thereby causing external air to be drawn into proximity of sensor 20 in cavity 36 via opening 26 of port 28. By enhancing airflow into cavity 36 adjacent to sensor 20, the response time of sensor 20 can be decreased.

Figure 8:
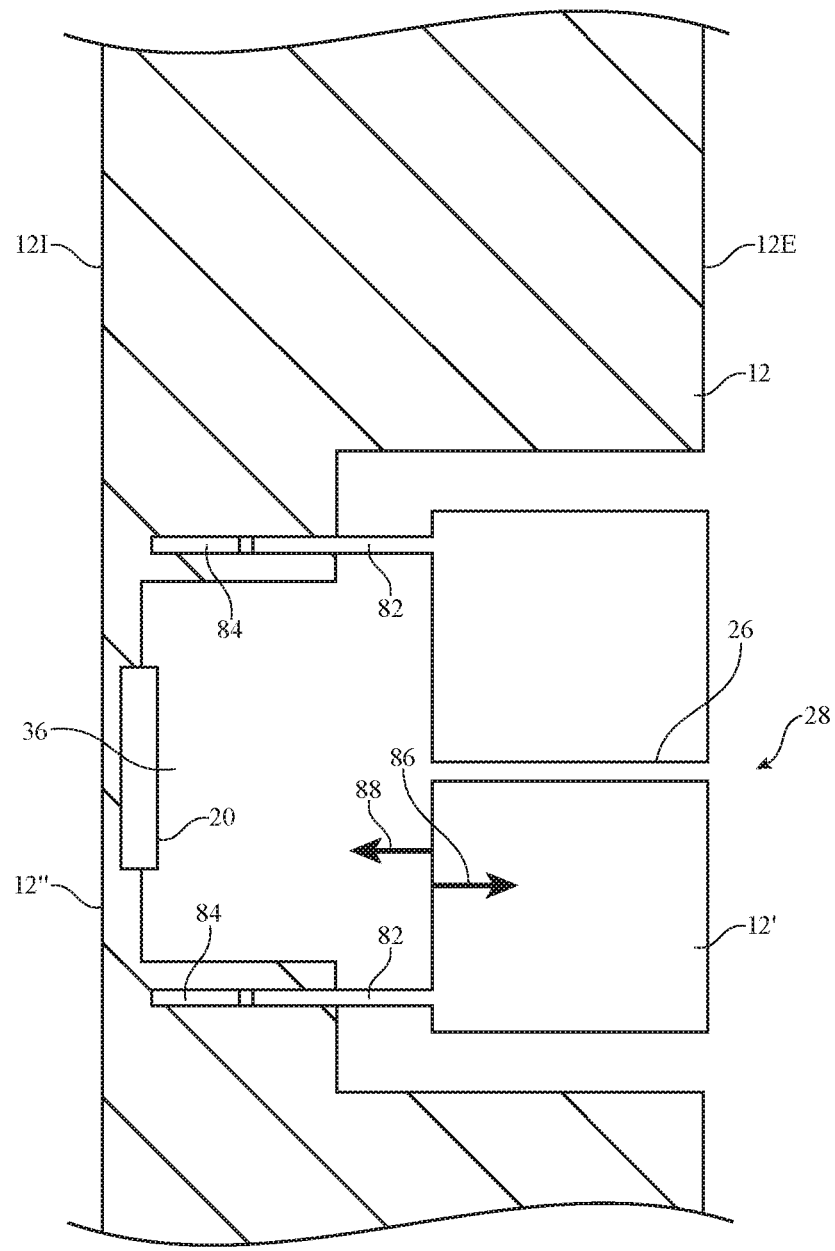
FIG. 8 is a cross-sectional side view of an illustrative housing wall to which a movable structure with a sensor port has been mounted to help promote airflow to a sensor in accordance with an embodiment.

Another illustrative configuration for enhancing the response of sensor 20 is shown in FIG. 8. In the illustrative configuration of FIG. 8, airflow through opening (channel) 26 of port 28 is enhanced by imparting movement to a member such as moving structure 12', while a support structure such as inner supporting portion 12" of wall 12 and sensor 20 remain stationary relative to the rest of device 10. Structure 12' may be a moving metal member or other moving structure and may have protrusions 82 that mate with recesses 84 in portion 12" or other structures that allow moving member 12' to slide in and out of housing 12 relative to portion 12" of the wall of housing 12 and sensor 20. Cavity 36 is formed in the space between moving member 12' and housing 12". When movement of device 10 causes portion 12' to move inwardly in direction 88 relative to housing structure 12", air will be expelled through opening 26 in moving member 12' and/or through other openings in chamber 36. When movement of device 10 causes structure 12' to move outwardly in direction 86, air will be drawn into cavity 36 through opening 26 and/or other passageways in sensor port 28, thereby providing fresh air for measurement by sensor 20.

Figure 9:
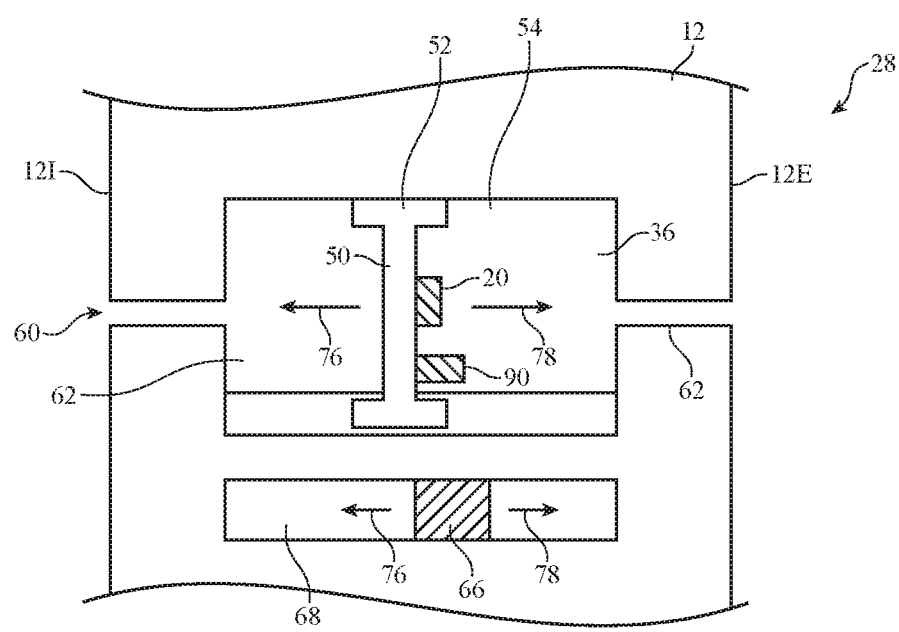
FIG. 9 is a cross-sectional side view of an illustrative housing wall in which a moving mass that is magnetically coupled to a moving member has been used to promote movement of the moving member and thereby enhance the flow of external air to a sensor in accordance with an embodiment.

FIG. 9 is a cross-sectional side view of a portion of device 10 in which moving weight 66 (see, e.g., moving weight 66 of FIG. 7) is magnetically coupled to movable member 50. Weight 66 may be, for example, a piece of samarium-cobalt, neodymium-iron-born, iron or other permanent magnetic material and a magnetically coupled structure such as permanent magnet 90 may be mounted to member 50. As movement of device 10 causes weight 66 to move in directions 76 and 78 within chamber 68, magnetic coupling between weight 66 and magnet 90 will impart corresponding movement to member 50 and sensor 20. In this way, airflow into cavity 36 will be enhanced and the response time of sensor 20 will be minimized. If desired, springs, gears, levers, flexible structures such as cords, and other structures may be used in addition to or instead of using magnetic coupling structures. Magnetic coupling structures may be formed from a pair of magnets, from a magnetic material such as iron that is magnetically coupled to a magnet, etc. Magnets may be formed on member 50 and/or in moving weight chamber 68 (e.g., weight 66 and/or member 50 may be formed from a magnet or a structure to which a magnet is attached and/or a magnetic material such as iron). The configuration of FIG. 9 is illustrative.

Figure 10:
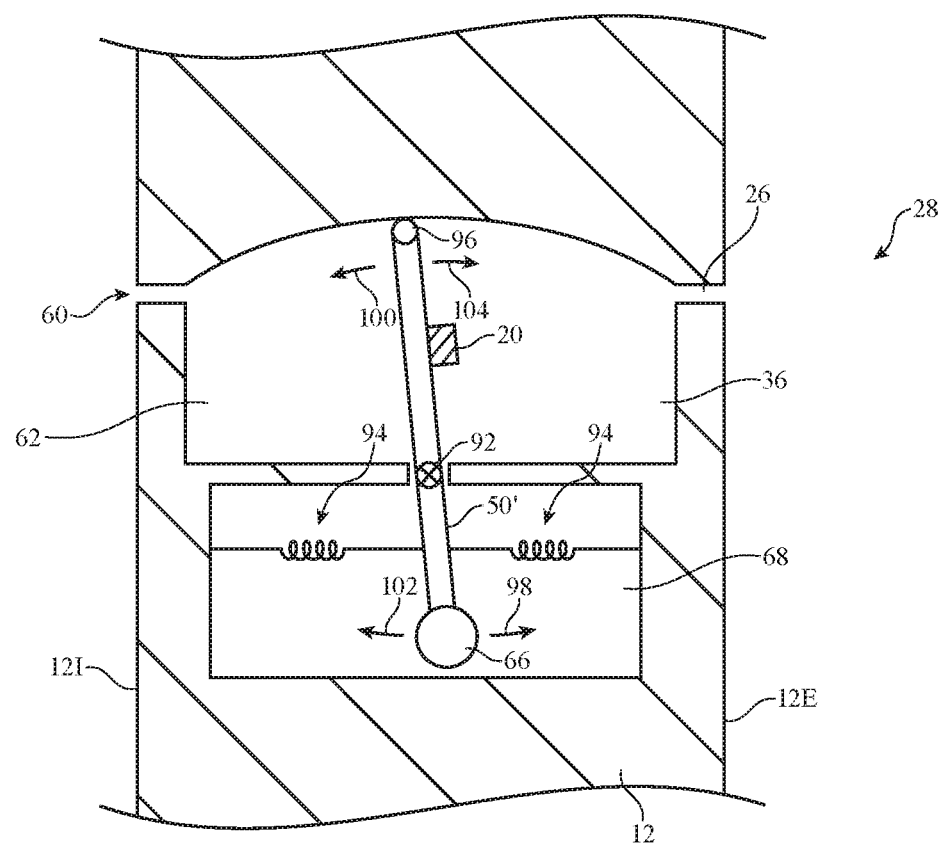
FIG. 10 is a cross-sectional side view of an illustrative movable structure that pivots about a hinge to promote airflow through a sensor port to a sensor in accordance with an embodiment.

FIG. 10 is a cross-sectional side view of illustrative coupling structures based on a pivot such as hinge 92. Hinge 92 may couple weight 66 in chamber 68 to moving member 50 in cavity 36. Member 50 may have an extended portion such as portion 50' that supports weight 66 and that couples weight 66 to member 50. Optional springs 94 may be coupled to the moving structures of FIG. 10 or other moving structures associated with sensor 20. Springs 94 may help provide stability against unwanted vibrations. Springs 94 may be omitted, if desired.

If desired, gasket structures (e.g., foam, elastomeric material, etc.) such as gasket 96 may be used to help seal member 50 against the inner surfaces of cavity 36 and thereby minimize air leakage that might reduce the effectiveness of movement of member 50 at promoting airflow through port 28. In the configuration of FIG. 10, movement of weight 66 in direction 98 will cause member 50 to move in direction 100 and movement of weight 66 in direction 102 will cause member 50 to move in direction 104 (i.e., member 50 and member portion 50' may pivot about hinge 92). Other arrangements for coupling motion of weight 66 to member 50 may be used if desired (e.g., the mass associated with weight 66 may be integrated into member 50, may be attached to the rear or front of member 50, etc.). The configuration of FIG. 10 is presented as an example.

Figure 11:
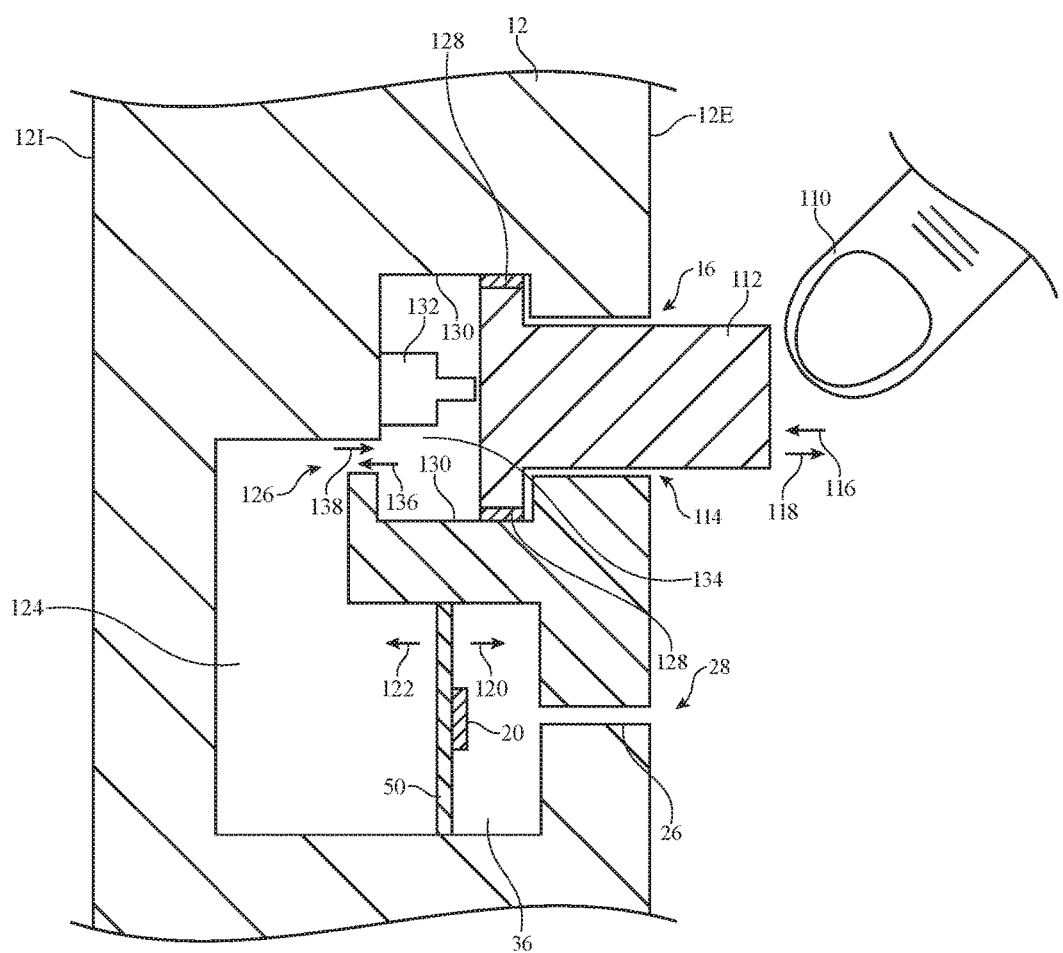
FIG. 11 is a cross-sectional side view of an illustrative electronic device in which movement of a movable member such as a button member is used to promote airflow through a sensor port to a sensor in accordance with an embodiment.

If desired, airflow through sensor port 28 may be enhanced due to movement of a button or other moveable member that is actuated by a user. Consider, as an example, the illustrative configuration of FIG. 11. In the example of FIG. 11, button 16 is mounted on the side of housing 12. Button 16 may include a moving structure such as button member 112. Button member 112 may move within opening 114 in the wall of housing 12. Button member 112 may move inwardly against switch 132 in direction 116 when pressed by user's finger 110, thereby activating switch 132. Switch 132 may include a spring, a resilient dome, or other biasing structures. When finger 110 is released, switch 132 may expand and move member 112 back in outwards direction 118.

The inner surface of button member 112 may be adjacent to cavity 134. Gasket 128 or other sealing structure may, if desired, help seal the edges of button member 112 against inner cavity surface 130 of cavity 134. When button member 112 is moved in direction 116, air from cavity 134 may be forced in direction 136 through opening 126. Opening 126 allows cavity 134 to communicate with cavity 124 at the rear of moving member 50. When air is forced into cavity 124 through opening 126, moving member 50 will be forced outwardly in direction 120. This expels air from cavity 36 to the exterior of device 10 through opening 26 of sensor port 28. When button 112 is released, switch 132 (or ancillary springs or other biasing structures) may force button member 112 in direction 118, thereby drawing air from cavity 124 into cavity 134 in direction 138 via opening 126. This creates a drop in air pressure in cavity 124 and moves member 50 inwardly in direction 122. The inward movement of member 50 in direction 122 draws fresh air into cavity 36 adjacent to sensor 20 through sensor port 28 and thereby helps reduce the response time of sensor 20.

If desired, other structures may be used to couple button motion due to user finger pressure to movement of wall 50 (e.g., button member 112 or other structures in button 16 may be coupled to member 50 with a rigid coupling structure, with a cable-based coupling structure or other flexible coupling structure, using magnetic coupling, using a lever structure of the type shown in FIG. 10, etc.). Moreover, moving weights and structures of the type shown in FIGS. 5-10 may, if desired, be used in conjunction with a moving button structure to promote airflow through sensor port 28. The configuration of FIG. 11 in which button motion is used to create air pressure gradients that move member 50 is merely illustrative.

The foregoing is merely illustrative and various modifications can be made by those skilled in the art without departing from the scope and spirit of the described embodiments. The foregoing embodiments may be implemented individually or in any combination.

What is claimed is:

1. An electronic device that may be moved when handled by a user, comprising:
    a housing;
    a sensor in the housing;
    a sensor port in the housing that allows the sensor to communicate with external air surrounding the housing; and
    a moving member that moves relative to the housing in response to motion of the electronic device due to handling by the user, wherein motion of the moving member promotes airflow through the sensor port and wherein the sensor is mounted to the moving member.

2. The electronic device defined in claim 1 wherein the sensor port includes a channel and a porous structure to block environmental contaminants and wherein motion of the moving member promotes airflow through the channel and the porous structure.

3. The electronic device defined in claim 1 further comprising a moving weight that moves within a moving weight chamber and that helps move the moving member.

4. The electronic device defined in claim 3 further comprising a coupling structure that couples the moving weight to the moving member.

5. The electronic device defined in claim 4 wherein the coupling structure comprises a flexible structure.

6. The electronic device defined in claim 4 wherein the moving weight is magnetically coupled to the moving member.

7. The electronic device defined in claim 1 wherein the moving member has protrusions that mate with grooves in the housing.

8. The electronic device defined in claim 1 further comprising a hinge, wherein the moving member is coupled to the hinge and pivots about the hinge.

9. The electronic device defined in claim 1 wherein the housing surrounds a first cavity portion and a second cavity portion, wherein the moving member separates the first cavity portion from the second cavity portion, wherein the first cavity portion is coupled to the sensor port, and wherein the housing has an opening that allows air to flow out of the second cavity portion when the external air flows into the first cavity portion through the sensor port.

10. The electronic device defined in claim 1 wherein the sensor comprises an environmental sensor.

11. The electronic device defined in claim 1 wherein the sensor comprises a sensor selected from the group consisting of: a temperature sensor, a humidity sensor, a gas composition sensor, and a particulate sensor.

12. The electronic device defined in claim 11 further comprising a button, wherein motion of the button promotes motion of the moving member.

13. A portable electronic device, comprising:
    a housing;
    a sensor in the housing;
    a sensor port in the housing through which the sensor communicates with external air surrounding the housing while the sensor makes measurements on the external air; and
    a moving member that moves relative to the housing and thereby promotes airflow through the sensor port wherein the moving member has protrusions that mate with grooves in the housing.

14. The portable electronic device defined in claim 13 wherein the sensor comprises a sensor selected from the group consisting of: a temperature sensor, a humidity sensor, a gas composition sensor, and a particulate sensor.

15. The portable electronic device defined in claim 14 wherein the moving member is configured to move in response to movement of the housing from handling by a user.

16. The portable electronic device defined in claim 14 further comprising a button, wherein motion of the button moves the moving member.

17. An electronic device that is moved by a user, comprising:
    a housing structure, wherein the housing structure surrounds a cavity having a first cavity portion and a second cavity portion;
    a sensor in communication with ambient air through a sensor port; and
    a movable structure that slides relative to the housing structure in response to movement of the electronic device by the user and thereby promotes flow of the ambient air through the sensor port to the sensor, wherein the moveable structure seals the first cavity portion from the second cavity portion while sliding relative to the housing structure.

18. The electronic device defined in claim 17 wherein the sensor comprises a sensor selected from the group consisting of: a temperature sensor, a humidity sensor, a gas composition sensor, and a particulate sensor.

19. The electronic device defined in claim 18 wherein the sensor port comprises an opening in the housing structure.

20. The electronic device defined in claim 17 wherein the first cavity portion is coupled to the sensor port and wherein the housing structure has an opening that allows air to flow out of the second cavity portion when the external air flows into the first cavity portion through the sensor port to prevent backpressure from developing in the second cavity portion.

* * * * *